(12) United States Patent
Takada et al.

(10) Patent No.: US 11,776,800 B2
(45) Date of Patent: Oct. 3, 2023

(54) SUBSTANCE ANALYZER AND SUBSTANCE ANALYSIS METHOD

(71) Applicant: Hitachi High-Tech Corporation, Tokyo (JP)

(72) Inventors: Yasuaki Takada, Tokyo (JP); Shun Kumano, Tokyo (JP); Masuyuki Sugiyama, Tokyo (JP); Tsukasa Shishika, Tokyo (JP); Shinji Yoshioka, Tokyo (JP); Akimasa Osaka, Tokyo (JP)

(73) Assignee: Hitachi High-Tech Corporation, Tokyo (JP)

( * ) Notice: Subject to any disclaimer, the term of this patent is extended or adjusted under 35 U.S.C. 154(b) by 146 days.

(21) Appl. No.: 17/619,693

(22) PCT Filed: Jun. 20, 2019

(86) PCT No.: PCT/JP2019/024551
§ 371 (c)(1),
(2) Date: Dec. 16, 2021

(87) PCT Pub. No.: WO2020/255346
PCT Pub. Date: Dec. 24, 2020

(65) Prior Publication Data
US 2022/0359182 A1  Nov. 10, 2022

(51) Int. Cl.
*H01J 49/04* (2006.01)
*H01J 49/00* (2006.01)

(52) U.S. Cl.
CPC ........ *H01J 49/0486* (2013.01); *H01J 49/004* (2013.01); *H01J 49/0409* (2013.01)

(58) Field of Classification Search
CPC ... H01J 49/0486; H01J 49/004; H01J 49/0409
(Continued)

(56) References Cited

U.S. PATENT DOCUMENTS 6,894,276 B1   5/2005 Takada et al.
2004/0124352 A1  7/2004 Kashima et al.
(Continued)

FOREIGN PATENT DOCUMENTS

JP   2004-212073 A   7/2004
JP   2004-301749 A   10/2004
(Continued)

OTHER PUBLICATIONS

Forbes, T.P. et al., "Broad spectrum infrared thermal desorption of wipe-based explosive and narcotic samples for trace mass spectrometric detection", Analyst, Aug. 7, 2017, 142/16, 3002-3010.
(Continued)

*Primary Examiner* — Nicole M Ippolito
(74) *Attorney, Agent, or Firm* — Volpe Koenig

(57) ABSTRACT

A substance analyzer that includes, to enhance selectivity of substance analysis, the following: a heater that heats a medium for collecting a chemical substance adhering to a surface of an inspection object; a mass spectrometer that performs tandem mass spectrometry of vapor derived from the chemical substance heated and vaporized by the heater from the medium; and a control device that causes the mass spectrometer to perform, based on a temperature of the medium in the heater, tandem mass spectrometry for the chemical substance that is vaporized at the temperature of the medium using the vapor sent from the heater to the mass spectrometer.

12 Claims, 14 Drawing Sheets

(58) Field of Classification Search
USPC .................... 250/281, 282, 283, 286, 287
See application file for complete search history.

(56) References Cited

U.S. PATENT DOCUMENTS

| | | |
|---|---|---|
| 2004/0195499 A1 | 10/2004 | Ishikawa et al. |
| 2005/0061964 A1 | 3/2005 | Nagano et al. |
| 2005/0067565 A1 | 3/2005 | Takada et al. |
| 2008/0161393 A1* | 7/2008 | Barrett .................... A61P 25/06 |
| | | 514/484 |
| 2012/0222153 A1* | 8/2012 | Cui ...................... C12Q 1/6895 |
| | | 536/23.6 |
| 2022/0344140 A1* | 10/2022 | Takahashi ........... H01J 49/0495 |

FOREIGN PATENT DOCUMENTS

| | | |
|---|---|---|
| JP | 2005-098706 A | 4/2005 |
| JP | 2005-108578 A | 4/2005 |
| JP | 3894118 B2 | 3/2007 |
| JP | 2007-139551 A | 6/2007 |
| JP | 2016-173332 A | 9/2016 |

OTHER PUBLICATIONS

International Search Report, PCT/JP2019/024551, dated Sep. 3, 2019, 2 pgs.

\* cited by examiner

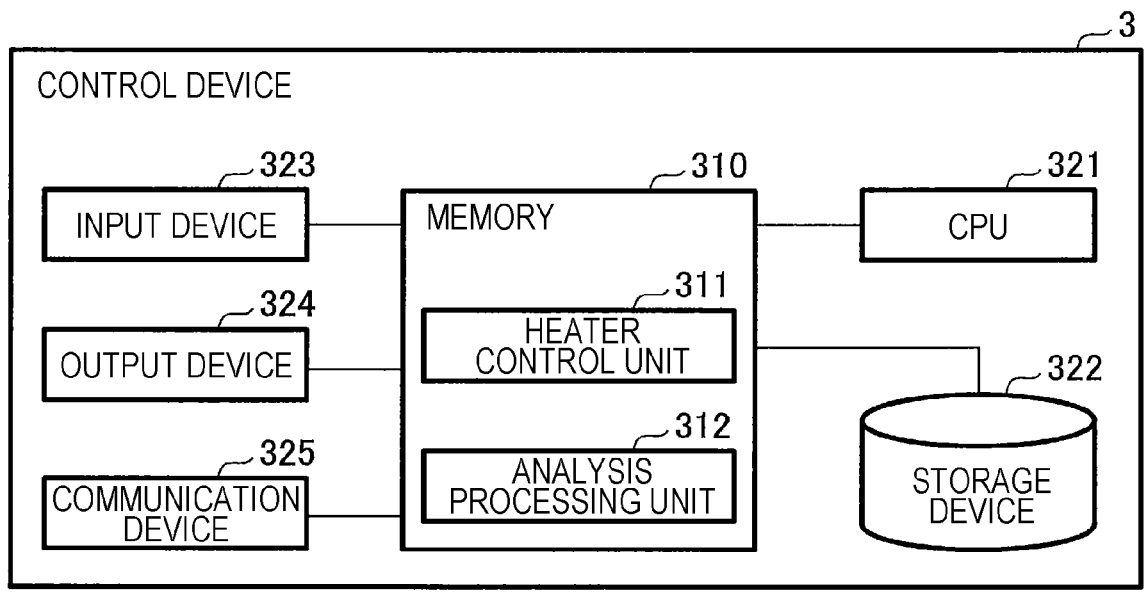

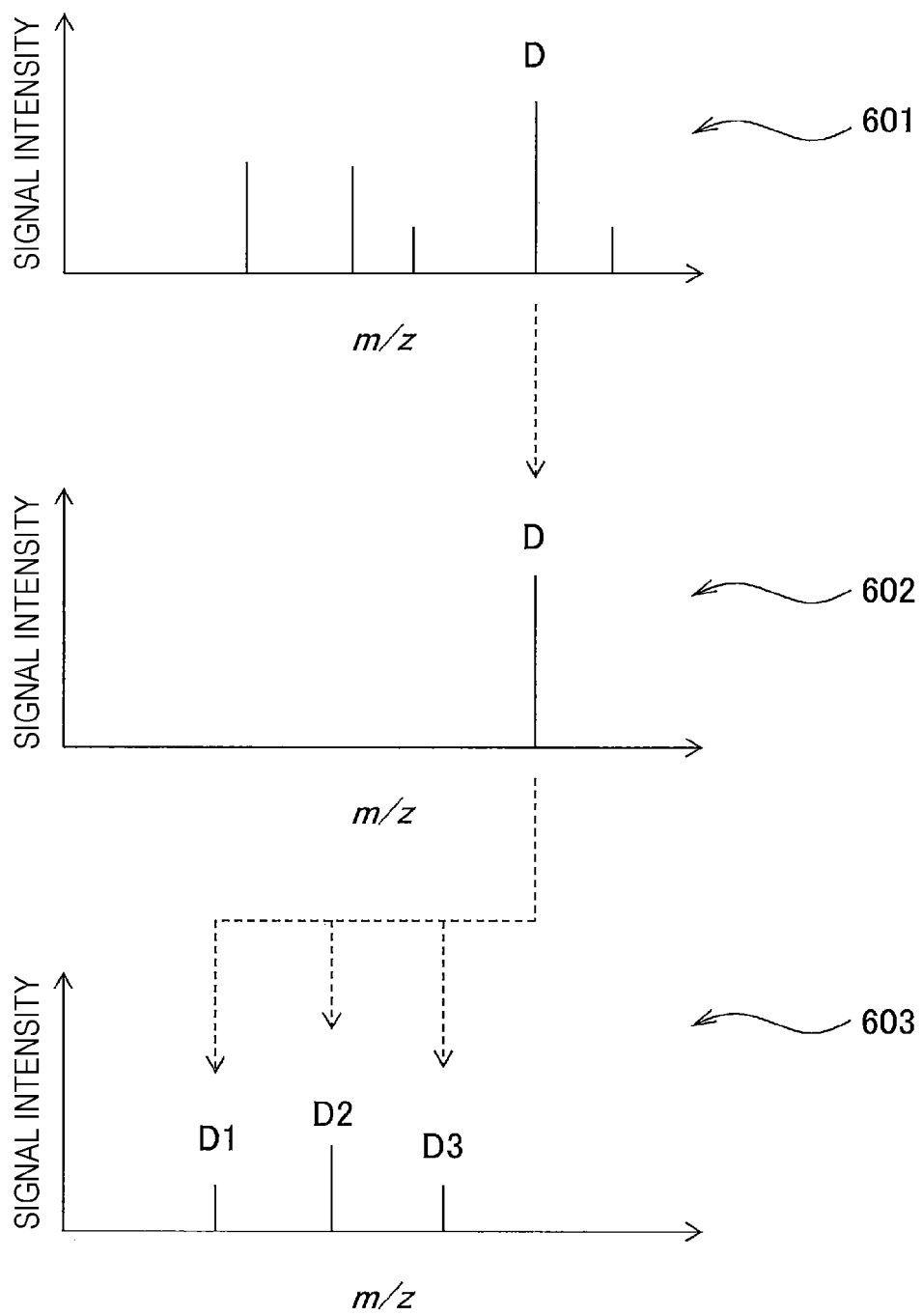

SUBSTANCE ANALYZER AND SUBSTANCE ANALYSIS METHOD

CROSS-REFERENCE STATEMENT

The present application is a U.S. National Stage, under U.S.C. § 371, of International Application Number PCT/JP2019/024551, filed Jun. 20, 2019, the disclosure of which is hereby incorporated by reference herein in its entirety.

TECHNICAL FIELD

The present invention relates to a technology of a substance analyzer and a substance analysis method.

BACKGROUND ART

The threat of terrorism is increasing worldwide. Increasingly, explosives are being used in acts of terrorism due to the spread of information via the Internet on methods of producing powerful explosives from common household items. One effective means of preventing explosives terrorism is to find hidden explosives with an explosive detection system. Two methods for detecting explosives are known: bulk detection for finding a mass of explosives; and trace detection for finding traces of minute explosives. Information obtained by bulk detection and trace detection is different, and bulk detection and trace detection can be operated in a complementary manner. Therefore, security can be improved by using both detection methods in combination.

In general, bulk detection represented by an X-ray inspection apparatus relies mainly on a shape of a suspicious object or the like. With bulk detection, it is difficult to identify a substance. Trace detection on the other hand is good at identifying a substance because a signal derived from a chemical substance can be detected by a chemical analysis method. For this reason, a detection device used for trace detection is expected to have high selectivity for accurately recognizing explosives without causing false alarms to be issued.

Among chemical analyses, a technique called tandem mass spectrometry is used as an analysis unit of a trace detection device because high selectivity can be obtained.

For example, Patent Literature 1 discloses a detection method and a detection device using an ion-trap mass spectrometer: "A detection method using an ion-trap mass spectrometer, comprising: a first analysis step of acquiring a mass spectrum; a first determination step of determining whether first unique m/z ions are present; a step of reading an analysis condition from a database according to a determination result of the first determination step; a second analysis step of performing tandem mass spectrometry; and a second determination step of determining whether second unique m/z ions are present" (see claim 1).

In addition, Patent Literature 2 discloses a mass spectrometer which "includes a means for controlling selection of a plurality of precursor ions by applying a high frequency signal not including resonance frequencies of a plurality of precursor ions but including resonance frequencies of other ions and having a different amplitude for each frequency to an electrode constituting an ion-trap mass spectrometer; and a means for controlling dissociation of a plurality of precursor ions by applying a high frequency signal having an amplitude individually set for each resonance frequency of the plurality of precursor ions and obtained by superimposing the resonance frequencies of the plurality of precursor ions to the electrode, and determines the presence or absence of a desired chemical substance based on a mass spectrum of a plurality of fragment ions obtained by dissociating the plurality of precursor ions" (see Abstract).

CITATION LIST

Patent Literature

Patent Literature 1: Japanese Patent No. 3894118
Patent Literature 2: Japanese Unexamined Patent Application Publication No. 2005-108578

SUMMARY OF INVENTION

Technical Problem

As described above, since the threat of terrorism is increasing, a detector with higher performance is required. From such a background, it is required to further improve selectivity with respect to the techniques described in Patent Literatures 1 and 2.

The present invention has been made in view of such a background, and an object of the present invention is to improve selectivity of substance analysis.

Solution to Problem

In order to solve the above problems, the present invention includes: a medium heater configured to heat a medium for collecting a chemical substance adhering to a surface of an inspection object; a tandem mass spectrometer configured to perform tandem mass spectrometry of vapor derived from the chemical substance sent from the medium by being heated and vaporized by the medium heater; and a controller configured to cause the tandem mass spectrometer to perform, based on a temperature of the medium in the medium heater, the tandem mass spectrometry for the chemical substance that is vaporized at the temperature of the medium using the vapor sent from the medium heater to the tandem mass spectrometer.

Other solutions will be appropriately described in the embodiments.

Advantageous Effects of Invention

According to the present invention, the selectivity of substance analysis can be enhanced.

BRIEF DESCRIPTION OF DRAWINGS

FIG. 6 is a functional block diagram illustrating a configuration of a control device used in the first embodiment.

FIG. 7 is a diagram illustrating a configuration of analysis timing information used in the first embodiment.

FIG. 8 is a diagram illustrating a concept of tandem mass spectrometry.

DESCRIPTION OF EMBODIMENTS

Next, modes for carrying out the present invention (referred to as "embodiments") will be described in detail with reference to the drawings as appropriate.

First Embodiment

System

Figure 1:
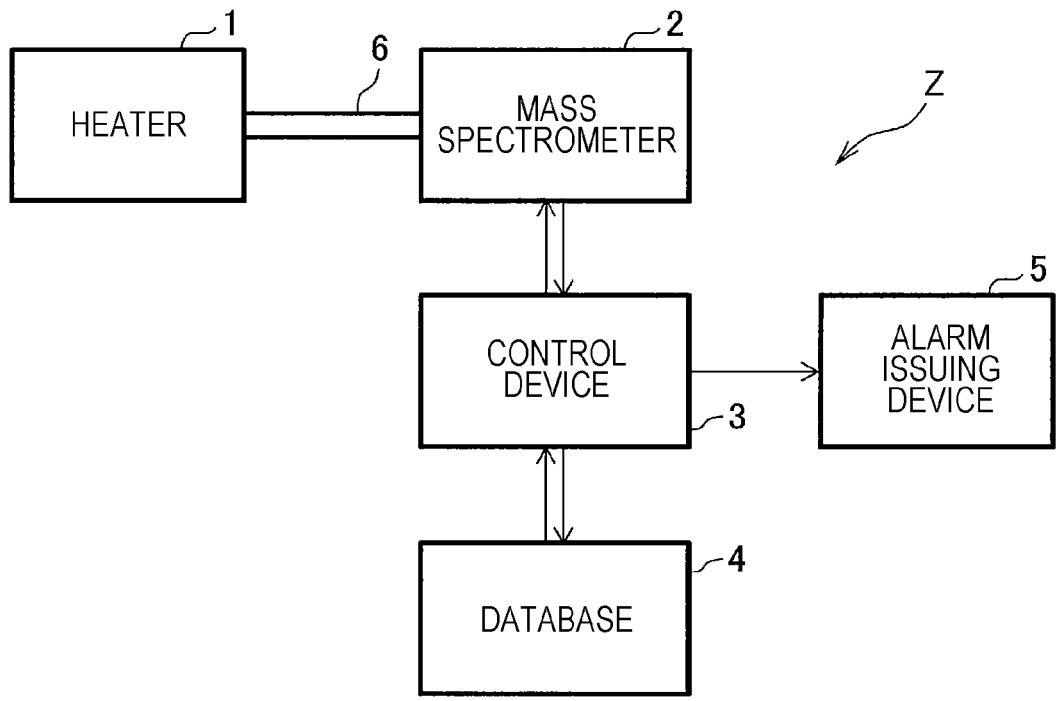
FIG. 1 is a diagram illustrating a configuration of a dangerous object detection system according to a first embodiment.

FIG. 1 is a diagram illustrating a configuration of a dangerous object detection system Z according to a first embodiment.

The dangerous object detection system Z includes a heater 1, a mass spectrometer 2, a control device 3, a database 4, and an alarm issuing device 5.

The heater 1 is connected to the mass spectrometer 2 via a pipe 6. The control device 3 is connected to the heater 1, the mass spectrometer 2, the database 4, and the alarm issuing device via a signal line (solid arrow). In the dangerous object detection system Z, when an inspector inserts a wipe material W (see FIG. 2) that has been used to wipe an inspection target, such as a bag, into the heater 1, the control device 3 starts temperature control of the heater 1 so as to gradually increase the temperature of the wipe material W. The wipe material W is made of heat-resistant fiber.

Chemical substances adhering to the wipe material W are sent to the mass spectrometer 2 through the pipe 6 in order with the highest vapor pressure component that vaporizes even at a low temperature sent first. When the temperature rising conditions of the heater 1 are kept the same, the chemical substances having different vapor pressure conditions (vaporization temperatures) are vaporized from the wipe material W under the respective vapor pressure conditions (that is, the temperature of the heater 1) as the temperature of the heater 1 rises, with the insertion of the wipe material W as a starting point.

That is, when the temperature rise of the heater 1 is kept consistent, different chemical substances are vaporized from the wipe material W at different times. When the temperature rise of the heater 1 is kept consistent, it is possible to know which chemical substance is vaporized from the wipe material W at which timing.

Therefore, at the time when each substance reaches the mass spectrometer 2, an analysis condition for the tandem mass spectrometry corresponding to the substance is sent from the control device 3 to the mass spectrometer 2. Then, the mass spectrometer 2 performs tandem mass spectrometry under the sent analysis condition. The database 4 stores analysis timing information 401 (see FIG. 7) in which a time from the insertion of the wipe material W into the heater 1 is associated with a chemical substance to be subjected to tandem mass spectrometry. In addition, the database 4 stores results (preliminary analysis information) of tandem mass spectrometry of various explosives.

The analysis result by the mass spectrometer 2 is collated with the preliminary analysis information in the database 4 by the control device 3. Then, when a desired signal is obtained, it is regarded that an explosive has been detected, and an alarm is issued by the alarm issuing device 5.

Heater 1

Figure 2:
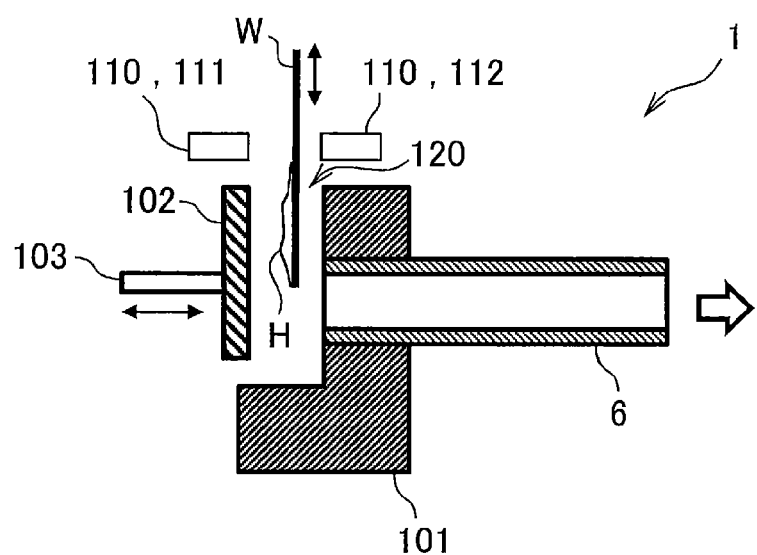
FIG. 2 is a sectional view of a heater used in the first embodiment.
Figure 3:
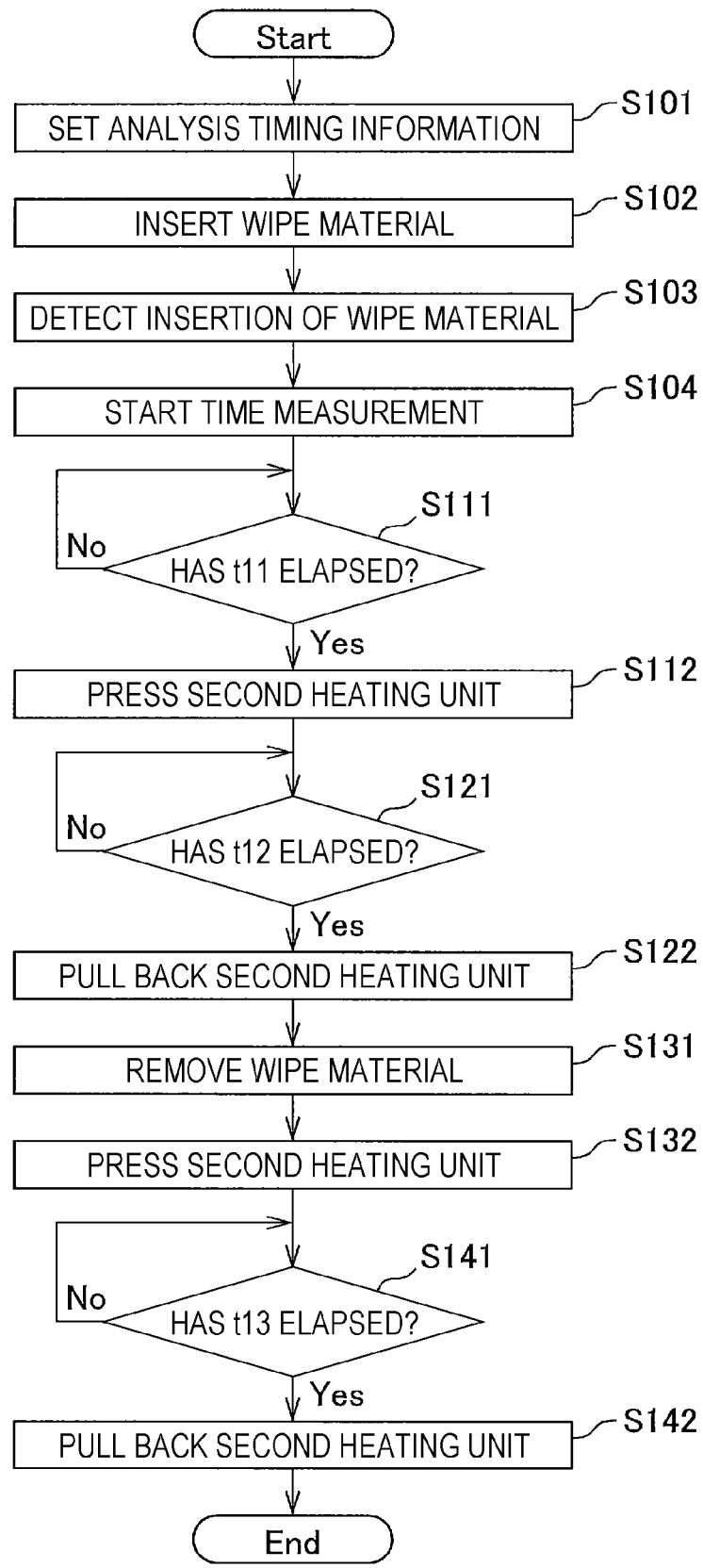
FIG. 3 is a flowchart illustrating an operation procedure of the heater.

FIG. 2 is a sectional view of the heater 1 used in the first embodiment. FIG. 3 is a flowchart illustrating an operation procedure of the heater 1 illustrated in FIG. 2.

As illustrated in FIG. 2, the heater 1 includes a first heating unit 101, a second heating unit 102, a head unit drive unit 103, a sensor 110, and a pipe 6 connected to the mass spectrometer 2.

Hereinafter, each part of FIG. 2 will be described with reference to FIG. 3.

First, a user sets the analysis timing information 401 (S101).

Next, when the user inserts the wipe material W into the heater 1 (S102), the sensor 110 detects the insertion of the wipe material W (S103). The wipe material W is inserted into an insertion portion 120 (gap) formed between the first heating unit 101 and the second heating unit 102.

Then, a heater control unit 311 (see FIG. 6) of the control device 3 starts measuring time with the insertion of the wipe material W as a starting point (S104). As an example of the sensor 110, as illustrated in FIG. 2, it is conceivable that a light emitting portion 111 and a light receiving portion 112 are arranged to face each other so that a change in the amount of light received by the light receiving portion 112, due to light from the light emitting portion 111 being blocked by the wipe material W, may be measured. In the vicinity of the insertion portion 120, the first heating unit (low temperature portion) 101 that has been heated in advance to a desired temperature (for example, 100° C.) is provided. After the insertion of the wipe material W is detected, the wipe material W is heated by the heat of the first heating unit 101 for a desired time (for example, 5 seconds).

Next, the heater control unit 311 (see FIG. 6) determines whether time t11 has elapsed from the start of the time measurement of Step S104 (whether the elapsed time has reached t11) (S111).

When time t11 has not elapsed (No in S111), the heater control unit 311 returns the process to Step S111. During this time, the wipe material W is heated by the heat of the first heating unit 101.

When time t11 has elapsed (Yes in S111), the heater control unit 311 controls the head unit drive unit 103. As a result, the second heating unit (high temperature portion) 102 that has been heated in advance to a higher temperature (for example, 200° C.) than the first heating unit 101 is pressed against the wipe material W (S112). As a result, the wipe material W is further heated. A component attached to the wipe material W is vaporized by heat, and the obtained vapor is sent to the mass spectrometer 2 via the pipe 6.

The pipe 6 is desirably heated to about 180° C. in order to prevent adsorption of each component to the inner wall surface thereof. When the second heating unit 102 is pressed against the wipe material W, the heat of the second heating unit 102 is also transferred to the first heating unit 101. At this time, if the temperature of the first heating unit 101 rises, then the initial condition concerning temperature will change for the next wipe material W to be analyzed when it is inserted. Therefore, the heat capacity of the first heating unit 101 may be made larger than that of the second heating unit 102 to suppress the temperature rise of the first heating unit 101.

Next, the heater control unit 311 determines whether a predetermined time t12 has elapsed since the second heating unit 102 has been pressed against the wipe material W (S121).

When the predetermined time t12 has not elapsed (No in S121), the heater control unit 311 returns the process to Step S121.

When the predetermined time t12 has elapsed (Yes in S121), the heater control unit 311 pulls back the second heating unit 102 that had been pressed against the wipe material W (S122).

As described above, in the heater 1 illustrated in FIG. 2, the temperature of the wipe material W rises in two stages.

Next, the user removes the wipe material W from the heater 1 (S131).

Thereafter, the heater control unit 311 presses the second heating unit 102 against the first heating unit 101 without the wipe material W (S132). The removal of the wipe material W is detected by the sensor 110.

The meaning of the processing of Step S132 will be described below.

In the heater 1 illustrated in FIG. 2, a component having a low vapor pressure remains on the surface of the first heating unit 101 after the measurement is completed. When the next wipe material W to be analyzed is inserted, there is a possibility of the residual component affecting the analysis. In order to reliably remove such a residual component, after a wipe material W is removed, the heater control unit 311 presses the second heating unit 102 against the first heating unit 101 without the wipe material W. As a result, the surface of the first heating unit 101 is instantaneously heated, and the component remaining on the surface of the first heating unit 101 is vaporized and removed.

Next, the heater control unit 311 determines whether a predetermined time t13 has elapsed since the second heating unit 102 has been pressed against the first heating unit 101 (S141).

When the predetermined time t13 has not elapsed (No in S141), the heater control unit 311 returns the process to Step S141.

When the predetermined time t13 has elapsed (Yes in S141), the heater control unit 311 pulls back the second heating unit 102 that had been pressed against the first heating unit 101 (S142).

In the heater 1 illustrated in FIG. 2, it has been found by experiments that a better result is exhibited when the surface (wiping surface) of the wipe material W to which the attachable matter H is attached faces the second heating unit 102.

According to the configuration illustrated in FIG. 2, the temperature of the wipe material W can be raised stepwise with a simple configuration.

Temperature of Wipe Material W

Figure 4:
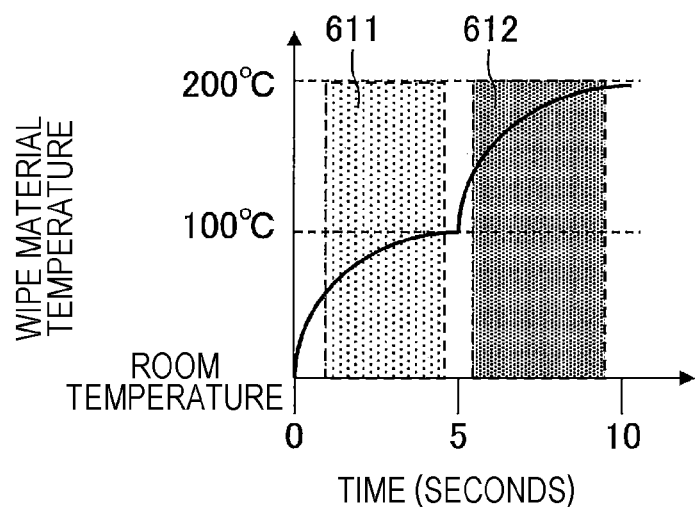
FIG. 4 is an image of a temperature change of a wipe material in the heater.

FIG. 4 is an image of a temperature change of the wipe material W in the heater 1 illustrated in FIG. 2.

In FIG. 4, the vertical axis represents the temperature of the wipe material W, and the horizontal axis represents time (seconds).

After the wipe material W is inserted into the heater 1, the wipe material W is heated to about 100° C. in about 5 seconds by heating (radiation and convection) by the first heating unit 101 (corresponding to the period of S111 in FIG. 3). At this time, among the chemical substances attached to the wipe material W, a chemical substance having a high vapor pressure, that is, easily vaporized, is vaporized (high vapor pressure component vaporization region 611). Subsequently, when the second heating unit 102 is pressed against the wipe material W (S112 in FIG. 3), the temperature of the wipe material W further increases, and a chemical substance having a low vapor pressure is also vaporized (low vapor pressure component vaporization region 612). By performing an experiment in advance, a temperature profile such as that illustrated in FIG. 4 may be obtained. The user sets the analysis timing information 401 based on such a temperature profile. In this way, a difference is provided in vaporization times of chemical substances according to a difference in vapor pressure of each chemical substance.

Mass Spectrometer 2

Figure 5:
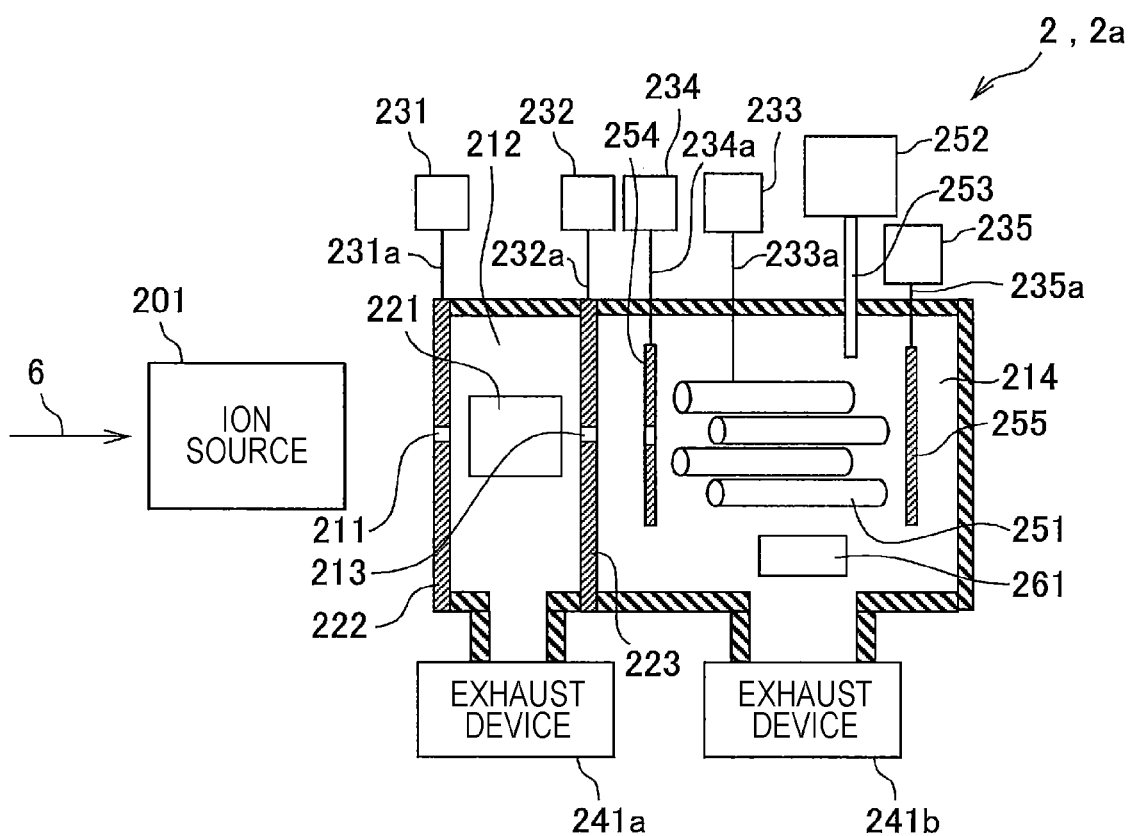
FIG. 5 is a diagram illustrating a configuration of an ion-trap mass spectrometer.

FIG. 5 is a diagram illustrating a configuration of an ion-trap mass spectrometer 2a.

There are various types of mass spectrometer 2. Here, it is assumed that the mass spectrometer 2 of an ion-trap method (ion-trap mass spectrometer 2a) as illustrated in FIG. 5 is used.

In the ion-trap mass spectrometer 2a, the chemical substance vaporized by the heater 1 is first sent to an ion source 201 via the pipe 6 and ionized. Ions generated by the ion source 201 are introduced into a vacuum portion 214 via a pore 211, a differential exhaust portion 212, and a pore 213. An ion guide 221 is provided in the differential exhaust portion 212 in order to increase the amount of ions introduced into the vacuum portion 214. In addition, in order to increase the amount of ions introduced into the vacuum portion 214, a voltage is applied from a power source 231 via a wiring 231a to an electrode with a pore 222 in which the pore 211 provides an opening. Similarly, a voltage is applied from a power source 232 via a wiring 232a to an electrode with a pore 223 in which the pore 213 provides an opening.

The differential exhaust portion 212 and the vacuum portion 214 are exhausted by exhaust devices 241a and 241b respectively. A mass spectrometry unit 251 that is disposed in the vacuum portion 214 includes four rods. A high frequency wave is applied to these rods from a power source 233 via a wiring 233a. To confine ions, the mass spectrometry unit 251 is supplied with a lean helium gas from a helium gas supply unit 252 through a helium gas supply pipe 253. Confinement electrodes 254 and 255 for creating an electric field for confining ions in the axial direction are disposed at both ends of the mass spectrometry unit 251. A voltage is applied to the electrode 254 from a power source 234 via a wiring 234a. Similarly, a voltage is applied to the electrode 255 from a power source 235 via a wiring 235a.

By changing the high-frequency voltage applied to the rods, trajectories of ions confined in the mass spectrometry unit 251 are destabilized in the ascending order of m/z and are discharged to the outside of the mass spectrometry unit

251. A mass spectrum is acquired by detecting the discharged ions by an ion detector 261.

Note that one ion-trap mass spectrometer 2a illustrated in FIG. 5 can perform tandem mass spectrometry and can also perform non-tandem mass spectrometry.

Note that the mass spectrometer 2 is not limited to the ion-trap mass spectrometer 2a as illustrated in FIG. 5 as long as the mass spectrometer can perform tandem mass spectrometry and non-tandem mass spectrometry.

Control Device 3

FIG. 6 is a functional block diagram illustrating a configuration of the control device 3 used in the first embodiment.

The control device 3 includes a memory 310, a central processing unit (CPU) 321, a storage device 322 such as a hard disk (HD), an input device 323 such as a keyboard and a mouse, an output device 324 such as a display, and a communication device 325 such as a network interface card (NIC).

Then, a program stored in the storage device 322 is loaded into the memory 310 and executed by the CPU 321. The heater control unit 311 and an analysis processing unit 312 are thus embodied.

The heater control unit 311 controls the heater 1.

The analysis processing unit 312 performs processing of tandem mass spectrometry or non-tandem mass spectrometry by the mass spectrometer 2.

Analysis Timing Information 401

FIG. 7 is a diagram illustrating a configuration of the analysis timing information 401 used in the first embodiment.

As illustrated in FIG. 7, the analysis timing information 401 stores elapsed times (t1, t2, t3, . . . ) and chemical substances ("Chemical substance A", "Chemical substance B", "Chemical substance C", . . . ) in association with each other. Here, the elapsed time is an elapsed time from the time when the wipe material W is inserted into the heater 1. That is, when time (heating time) t1 has elapsed since the insertion of a wipe material W, tandem mass spectrometry concerning "Chemical substance A" is performed. When time t2 has elapsed since the insertion of the wipe material W, tandem mass spectrometry concerning "Chemical substance B" is performed. When time t3 has elapsed since the insertion of the wipe material W, tandem mass spectrometry concerning "Chemical substance C" is performed.

Here, all of the times t1, t2, t3, . . . are elapsed times from the time when the wipe material W is inserted into the heater 1, but the present invention is not limited thereto. For example, when time t1 elapses from the insertion of the wipe material W, tandem mass spectrometry concerning "Chemical substance A" may be performed, and when time t2 elapses after completion of tandem mass spectrometry for "Chemical substance A", tandem mass spectrometry for "Chemical substance B" may be performed. Similarly, when time t3 elapses after completion of tandem mass spectrometry for "Chemical substance B", tandem mass spectrometry for "Chemical substance C" may be performed.

Tandem Mass Spectrometry

FIG. 8 is a diagram illustrating a concept of tandem mass spectrometry. When non-tandem mass spectrometry is performed, a so-called mass spectrum 601 in which a horizontal axis represents m/z (mass-to-charge ratio) and a vertical axis represents signal intensity as illustrated in the upper part of FIG. 8 is obtained.

In the mass spectrum 601 illustrated in FIG. 8, various signals such as ions derived from a desired chemical substance (in this case, "Chemical substance D") and ions derived from an organic substance contained in the atmosphere are displayed in an overlapping manner. For this reason, if there is an impurity present that happens to generate ions having the same m/z as ions derived from a desired chemical substance (an explosive in the present embodiment), there is a possibility of issuing an erroneous report. In the non-tandem mass spectrometry, the analysis ends at a stage where the mass spectrum 601 is obtained.

The ion-trap mass spectrometer 2a has a function of selecting ions of a desired m/z. As a result, when a mass spectrum is acquired after only ions having one m/z are selected, a simple mass spectrum as illustrated by the mass spectrum 602 is obtained. After ions of a desired m/z are selected, as illustrated in the mass spectrum 602, the ions are dissociated to acquire a mass spectrum that includes mass spectrums of a plurality of dissociated ions ("Chemical substance D1", "Chemical substance D2", and "Chemical substance D3") as illustrated in the mass spectrum 603. Here, desired dissociated ions generated from the ions of "Chemical substance D" are referred to as "Chemical substance D1" and "Chemical substance D2". Further, a dissociated ion generated from another ion (undesired ion) having the same m/z as the desired ion of "Chemical substance D" is defined as "Chemical substance D3". In the mass spectrum 603, each of "Chemical substance D1", "Chemical substance D2", and "Chemical substance D3" is separately displayed, so that selectivity is enhanced and erroneous reporting can be prevented.

Steps of Tandem Mass Spectrometry

Figure 9:
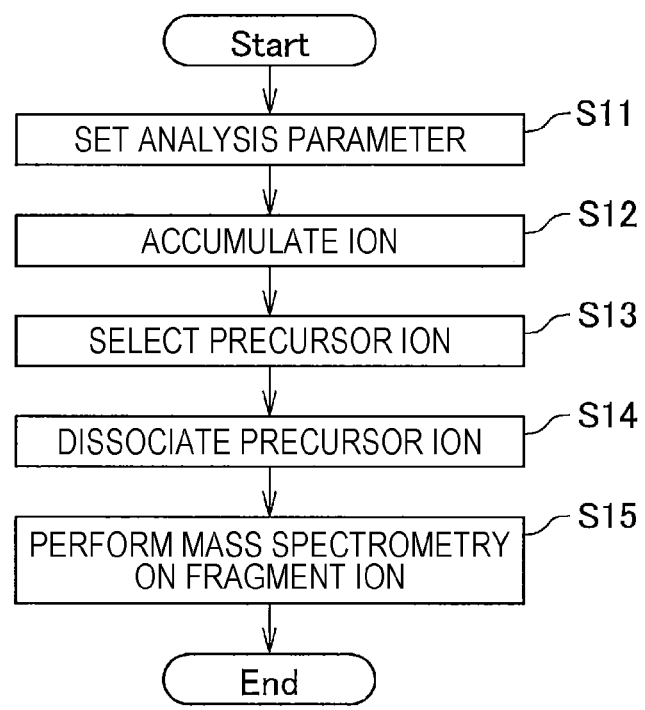
FIG. 9 is a flowchart illustrating steps of the tandem mass spectrometry by the ion-trap mass spectrometer.

FIG. 9 is a flowchart illustrating steps of tandem mass spectrometry by the ion-trap mass spectrometer 2a illustrated in FIG. 5.

First, before describing a specific procedure of tandem mass spectrometry, an outline of tandem mass spectrometry will be described. Ions trapped in the mass spectrometry unit 251 of the ion-trap mass spectrometer 2a illustrated in FIG. 5 vibrate in the mass spectrometry unit 251 at a frequency corresponding to m/z. Therefore, when a voltage having a frequency corresponding to an m/z of trapped ions is applied to the rod constituting the mass spectrometry unit 251, ions having the m/z can be accelerated.

Hereinafter, specific steps of tandem mass spectrometry will be described. The process illustrated in FIG. 9 is a general tandem mass spectrometry process. The process is not limited to the process illustrated in FIG. 9 as long as tandem mass spectrometry can be performed.

First, analysis parameters for tandem mass spectrometry of a chemical substance to be analyzed are set (S11). Here, the analysis parameters are information including a voltage applied to the rod to select precursor ions of a chemical substance to be analyzed, a frequency, or the like.

Then, ions generated by the ion source 201 are introduced into the mass spectrometry unit 251. Since a dilute helium gas is introduced into the mass spectrometry unit 251, ions introduced into the mass spectrometry unit 251 lose momentum due to collision with the helium gas and become trapped in the mass spectrometry unit 251. As a result, ions are accumulated in the mass spectrometry unit 251 (S12). When mass spectrometry is performed in the state of Step S12, non-tandem mass spectrometry is performed.

Next, a voltage (a type of white noise) not including a frequency that resonates with m/z of precursor ions but including many frequencies that resonate with other ions is applied to the rod constituting the mass spectrometry unit 251. As a result, precursor ions remain in the mass spectrometry unit 251, and other ions are removed. As a result, ions (precursor ions) to be dissociated are selected (S13).

Subsequently, a frequency resonating with m/z of the precursor ions is applied to the rod constituting the mass spectrometry unit 251 with a small amplitude, so that the precursor ions dissociate through collision with the helium gas (S14). Fragment ions are generated by dissociation of precursor ions.

Finally, mass spectrometry of the ions (fragment ions) obtained by dissociating the precursor ions is performed (S15).

Analysis

Figure 10:
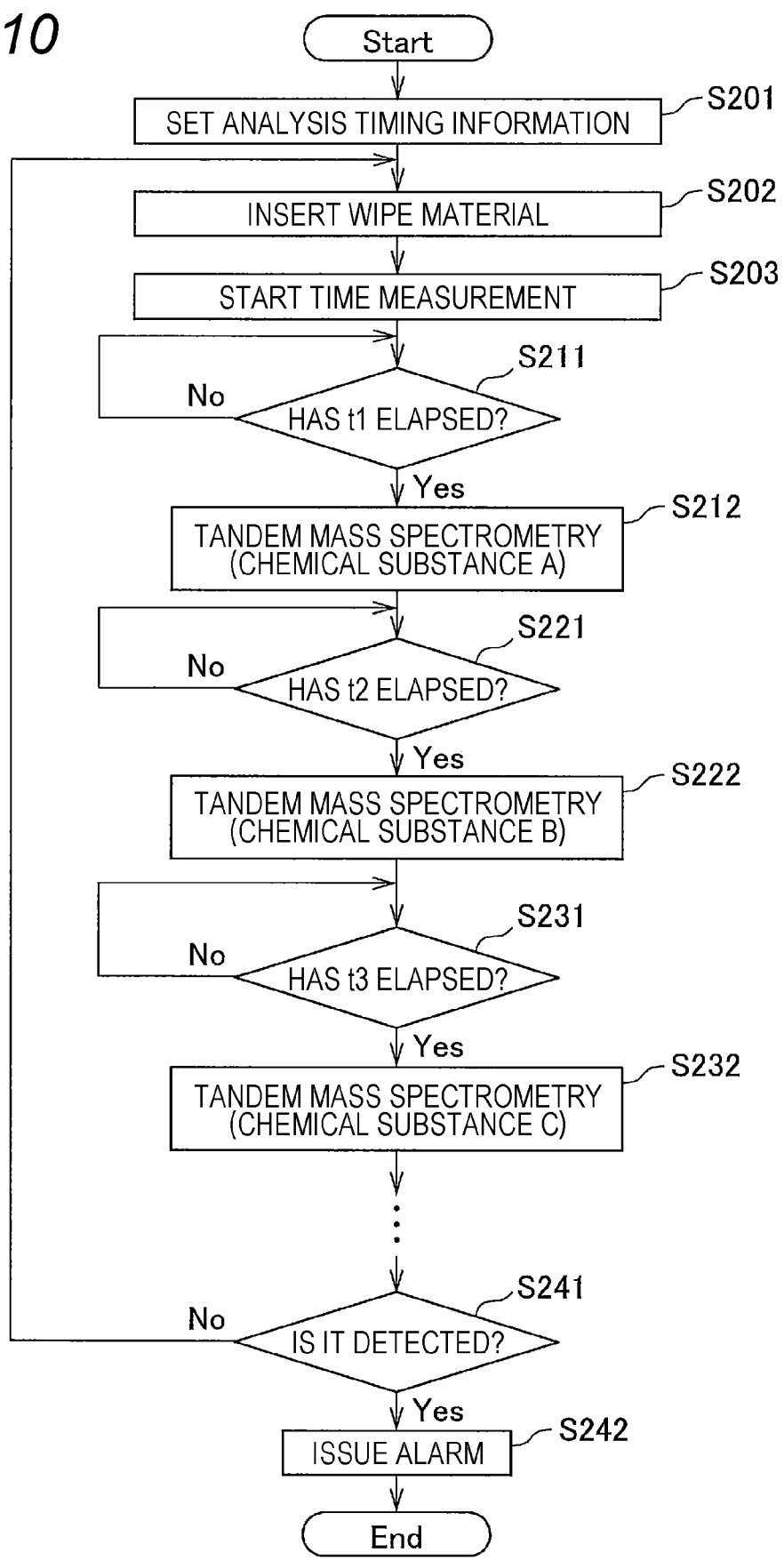
FIG. 10 is a flowchart illustrating a procedure of analysis performed in the first embodiment.

FIG. 10 is a flowchart illustrating a procedure of analysis performed in the first embodiment.

The user sets the analysis timing information 401 in advance (S201).

Next, a wipe material W (see FIG. 2) that has been used to wipe a surface of an object under inspection is inserted into the heater 1 by the user (S202). Then, the analysis processing unit 312 of the control device 3 starts measuring the heating time with the insertion of the wipe material W as a starting point (S203).

Note that Steps S201 to S203 are processes corresponding to Steps S101 to S104 in FIG. 3.

Thereafter, the analysis processing unit 312 determines whether time has elapsed for the time (heating time) from the start of the time measurement of Step S203 to reach time t1 at which "Chemical substance A" is measured (whether the elapsed time has reached t1) (S211). This determination is performed by the analysis processing unit 312 referring to the analysis timing information 401 illustrated in FIG. 7.

When time t1 has not elapsed (No in S211), the analysis processing unit 312 returns the process to Step S211.

When time t1 has elapsed (Yes in S211), the analysis processing unit 312 instructs tandem mass spectrometry for "Chemical substance A". The mass spectrometer 2 having received the instruction performs tandem mass spectrometry for "Chemical substance A" (S212).

Thereafter, the analysis processing unit 312 determines whether time has elapsed for the time from the start of the time measurement of Step S203 to reach time t2 at which "Chemical substance B" is measured (whether the elapsed time has reached t2) (S221). This determination is performed by the analysis processing unit 312 referring to the analysis timing information 401 illustrated in FIG. 7.

When time t2 has not elapsed (No in S221), the analysis processing unit 312 returns the process to Step S221.

When time t2 has elapsed (Yes in S221), the analysis processing unit 312 instructs tandem mass spectrometry for "Chemical substance B". The mass spectrometer 2 having received the instruction performs tandem mass spectrometry for "Chemical substance B" (S222).

Thereafter, the analysis processing unit 312 determines whether time has elapsed for the time from the start of the time measurement of Step S203 to reach time t3 at which "Chemical substance C" is measured (whether the elapsed time has reached t3) (S231). This determination is performed by the analysis processing unit 312 referring to the analysis timing information 401 illustrated in FIG. 7.

When time t3 has not elapsed (No in S231), the analysis processing unit 312 returns the process to Step S231.

When time t3 has elapsed (Yes in S231), the analysis processing unit 312 instructs tandem mass spectrometry for "Chemical substance C". The mass spectrometer 2 having received the instruction performs tandem mass spectrometry for "Chemical substance C" (S232).

Hereinafter, when time elapses to similarly reach a time for measuring another substance, tandem mass spectrometry is performed for the chemical substance that is vaporized from the wipe material W at that time. In this way, tandem mass spectrometry is repeated until the analysis that has been set is complete.

When tandem mass spectrometry is completed for all target chemical substances, the analysis processing unit 312 determines whether a signal indicating an explosive is detected from tandem mass spectrometry performed at any of the times (S241). This determination is performed by the control device 3 referring to preliminary analysis information stored in the database 4.

As a result of the determination, when a signal indicating an explosive is not detected (No in S241), the analysis processing unit 312 returns the process to Step S202.

As a result of the determination, when a signal indicating an explosive is detected (Yes in S241), the analysis processing unit 312 causes the alarm issuing device 5 to issue an alarm (S242). By doing so, it is possible to reliably notify the user that a chemical substance suspected of being an explosive has been detected.

As a specific example, by ionizing an explosive called trinitrotoluene by negative atmospheric pressure chemical ionization, an ion of m/z 227, which is a molecular ion of trinitrotoluene, is obtained. When tandem mass spectrometry is performed using this ion as a precursor ion, m/z 211 or the like in which oxygen is desorbed from trinitrotoluene is observed as a fragment ion. Therefore, m/z 227 is dissociated at the time when the precursor ion of trinitrotoluene appears, and the control device 3 determines whether ions such as m/z 211 are detected. This makes it possible to determine whether trinitrotoluene has adhered to the wipe material W.

Figure 11:
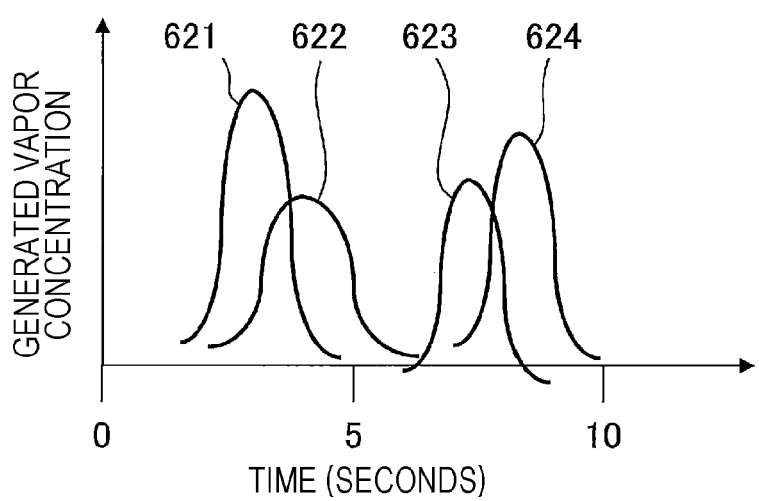
FIG. 11 schematically illustrates a temporal change of a generated vapor concentration.

FIG. 11 schematically illustrates a temporal change of the generated vapor concentration.

In FIG. 11, the vertical axis represents the vapor concentration generated, and the horizontal axis represents time (seconds). The temporal change of the vapor concentration illustrated in FIG. 11 is a result of using a heater 1c illustrated in FIG. 17.

The concentration of "Chemical substance A" having a high vapor pressure (reference numeral 621) is maximized relatively early in time. On the other hand, the concentration of "Chemical substance D" having a low vapor pressure (reference numeral 624) is maximized relatively late in time.

In addition, the concentration of "Chemical substance B" having the second highest vapor pressure (reference numeral 622) becomes maximum at the time next to "Chemical substance A". Furthermore, the concentration of "Chemical substance C" having the third highest vapor pressure (reference numeral 623) becomes maximum at the time next to "Chemical substance B".

As described above, by changing the temperature of the wipe material W in a plurality of stages, it is possible to provide a difference in time during which the concentration of the evaporating chemical substance increases. Then, at the timing when the concentration of each chemical substance increases, tandem mass spectrometry is performed under suitable analysis conditions for the component.

The dangerous object detection system Z according to the first embodiment performs tandem mass spectrometry of a substance vaporized from the heated wipe material W concerning a chemical substance set in advance for each heating time. By doing so, the selectivity can be enhanced. In the first embodiment, tandem mass spectrometry is performed based on a heating time (Times t1, t2, t3, . . . ). In this case the temperature of the wipe material W (in degrees centigrade) is judged using the elapse of the heating time.

Second Embodiment

Figure 12:
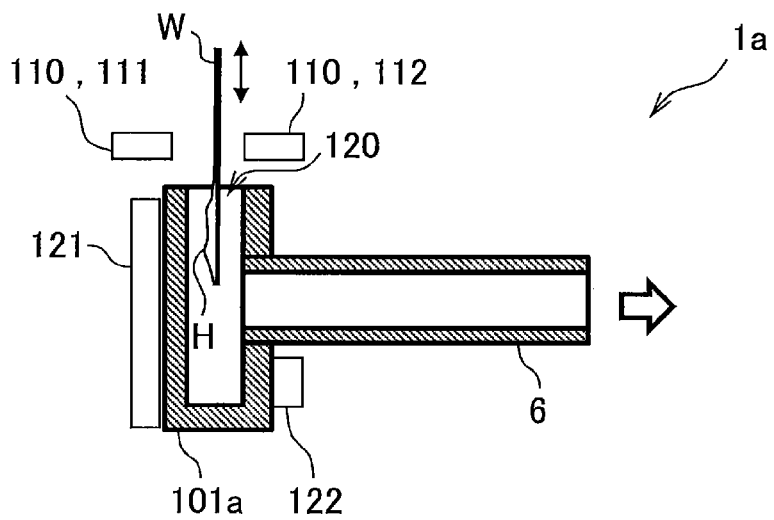
FIG. 12 is a sectional view of a heater used in a second embodiment.

FIG. 12 is a sectional view of a heater 1a used in a second embodiment.

In FIG. 12, the same components as those in FIG. 2 are denoted by the same symbols, and description thereof will be omitted.

In the heater 1a illustrated in FIG. 12, an electric heater 121 and a thermometer 122 are provided in a first heating unit 101a into which the wipe material W is inserted. Here, the first heating unit 101a has, for example, a tubular shape. When the wipe material W is inserted into the space of the insertion portion 120, the sensor 110 that senses the insertion of the wipe material W starts measuring the insertion time. In the vicinity of the insertion portion 120, the first heating unit 101a heated in advance to a desired temperature (for example, 100° C.) is provided. After the wipe material W is inserted into the first heating unit 101a, the wipe material W is heated by the heat of the first heating unit 101a for a desired time (for example, 5 seconds). After the desired time has elapsed, the temperature of the first heating unit 101a is gradually raised by the electric heater 121, and the temperature of the wipe material W is further raised. In this way, chemical substances attached to the wipe material W are sequentially vaporized starting from a component having the highest vapor pressure and introduced into the mass spectrometer 2 via the pipe 6. Then, tandem mass spectrometry corresponding to each chemical substance is performed. After all tandem mass spectrometry has been performed, the electric heater 121 is de-energized. Then, the user inserts the next wipe material W after confirming by the thermometer 122 that the temperature of the first heating unit 101a has returned to a predetermined temperature. In this case, the heat capacity of the first heating unit 101a may be reduced so that the temperature of the first heating unit 101a returns to the original temperature in a short time.

In the second embodiment, since the temperature of the wipe material W is easily estimated by the thermometer, the tandem mass spectrometry of a predetermined chemical substance may be managed by the temperature instead of being managed by time as illustrated in FIG. 7.

According to the configuration illustrated in FIG. 12, the temperature of the wipe material W can be raised in a plurality of stages.

Third Embodiment

Figure 13:
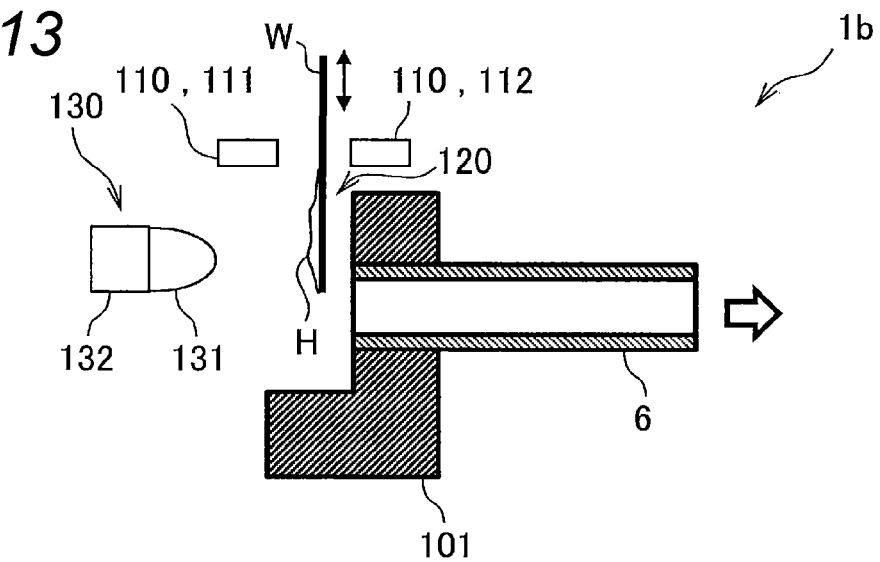
FIG. 13 is a sectional view of a heater used in a third embodiment.

FIG. 13 is a sectional view of a heater 1b used in a third embodiment.

In FIG. 13, the same components as those in FIG. 2 are denoted by the same symbols, and description thereof will be omitted.

The heater 1b illustrated in FIG. 13 includes an infrared device 130. The infrared device 130 includes an infrared lamp 131 that lights infrared rays and a power source 132 that supplies electric power to the infrared lamp 131.

When the user inserts the wipe material W into the insertion portion 120 of the heater 1b, the sensor 110 that senses the insertion of the wipe material W starts the insertion time. In the vicinity of the insertion portion 120, the first heating unit 101 heated in advance to a desired temperature (for example, 100° C.) is provided. After the insertion of the wipe material W, the wipe material W is heated by the heat of the first heating unit 101 for a desired time (for example, 5 seconds). After a desired time elapses, the heater control unit 311 connects the infrared lamp 131 to the power source 132 to turn on the infrared lamp 131. By irradiating the wipe material W with the infrared rays, the wipe material W is further heated. In this way, components attached to the wipe material W are sequentially vaporized starting from a component having the highest vapor pressure and introduced into the mass spectrometer 2 via the pipe 6. In the heater 1b illustrated in FIG. 13, when a material that easily absorbs infrared rays is used for the wipe material W, the temperature of the wipe material W can be rapidly increased, heat transfer to the first heating unit 101 is reduced, and the temperature rise of the first heating unit 101 can be suppressed. Since the wipe material W is irradiated with the infrared rays and the first heating unit 101 is not directly irradiated with the infrared rays, the temperature of the first heating unit 101 does not rise so much.

According to the configuration illustrated in FIG. 13, the temperature of the wipe material W can be raised in a plurality of stages.

Fourth Embodiment

In the first embodiment, as illustrated in FIG. 10, the timing of performing tandem mass spectrometry for each target chemical substance is defined by the time when that chemical substance is expected to be vaporized from the wipe material W and acquired by the mass spectrometer 2. By doing so, determination is made on whether or not the chemical substance that is vaporized and acquired at the timing is detected. The method of the first embodiment may be used to determine the presence or absence of an explosive. However, in the fourth embodiment, in order to confirm whether the mass spectrometer 2 is operating correctly, and the like, normal mass spectrometry is performed during the time when the tandem mass spectrometry is not executed as described below.

Specifically, when the surface of the inspection target (bag or the like) is very dirty with oil, paint, or the like, wiping the surface of the inspection target results in the adherence of excessive impurities on the wipe material W. When such excessive impurities are sent to the ion source 201 of the ion-trap mass spectrometer 2a as illustrated in FIG. 5, an excessive amount of ions is generated. In the ion-trap mass spectrometer 2a, when an excessive amount of ions are taken into the mass spectrometry unit 251, the electric field inside the mass spectrometry unit 251 changes due to the charge of the ions themselves. This may cause an adverse effect in the form of a decrease in resolution when the mass spectrum is acquired. In order to avoid such a phenomenon, in the fourth embodiment, normal mass spectrometry (non-tandem mass spectrometry) is performed during the time when the tandem mass spectrometry is not performed. By doing so, the mass spectrum is monitored, and when a phenomenon such as a decrease in resolution is observed, the performance of the ion-trap mass spectrometer 2a can be maintained by shortening the time of the step of accumulating ions or the like.

Figure 14A:
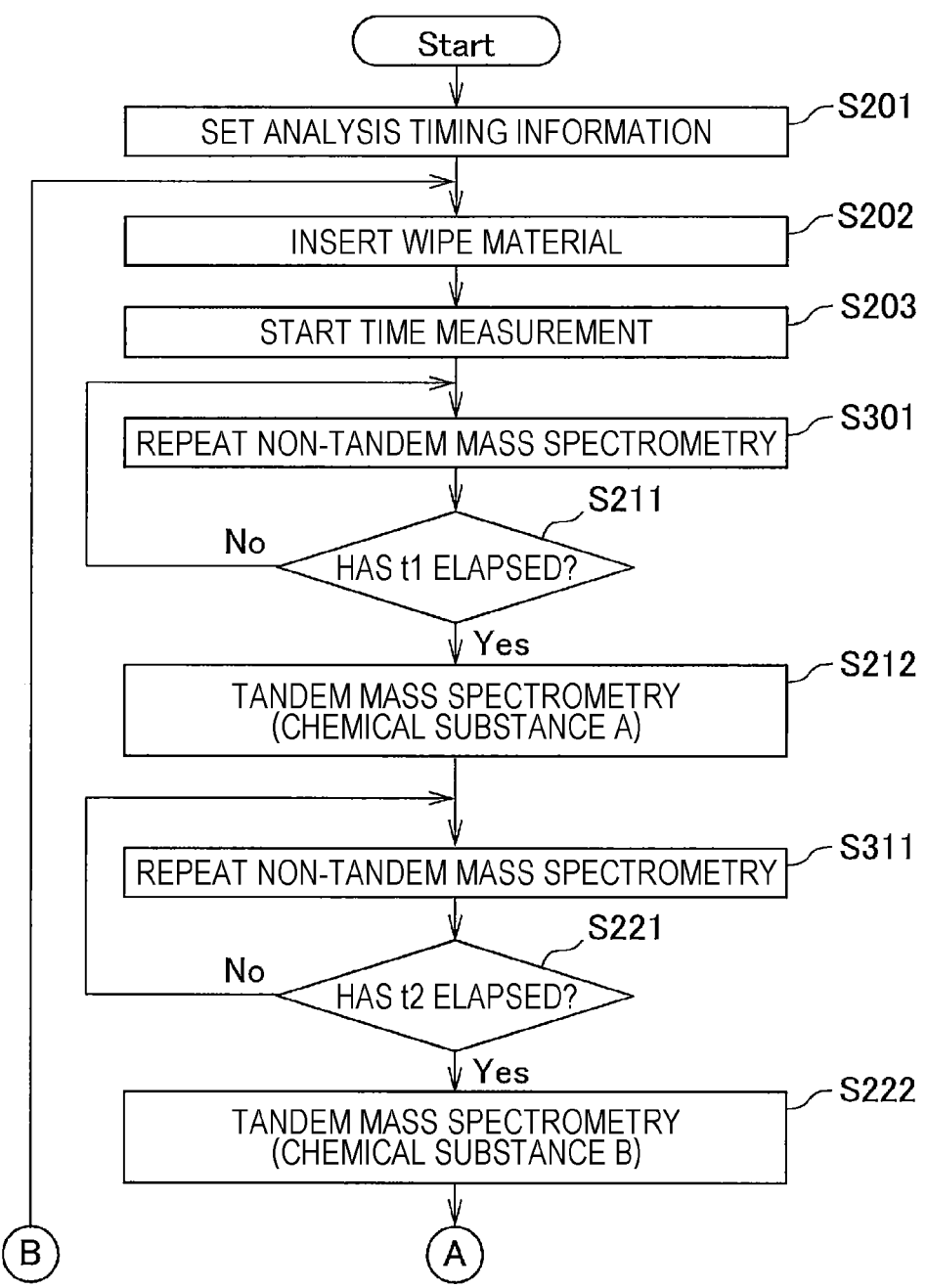
FIG. 14A is a flowchart (part 1) illustrating a procedure of analysis measurement performed in a fourth embodiment.
Figure 14B:
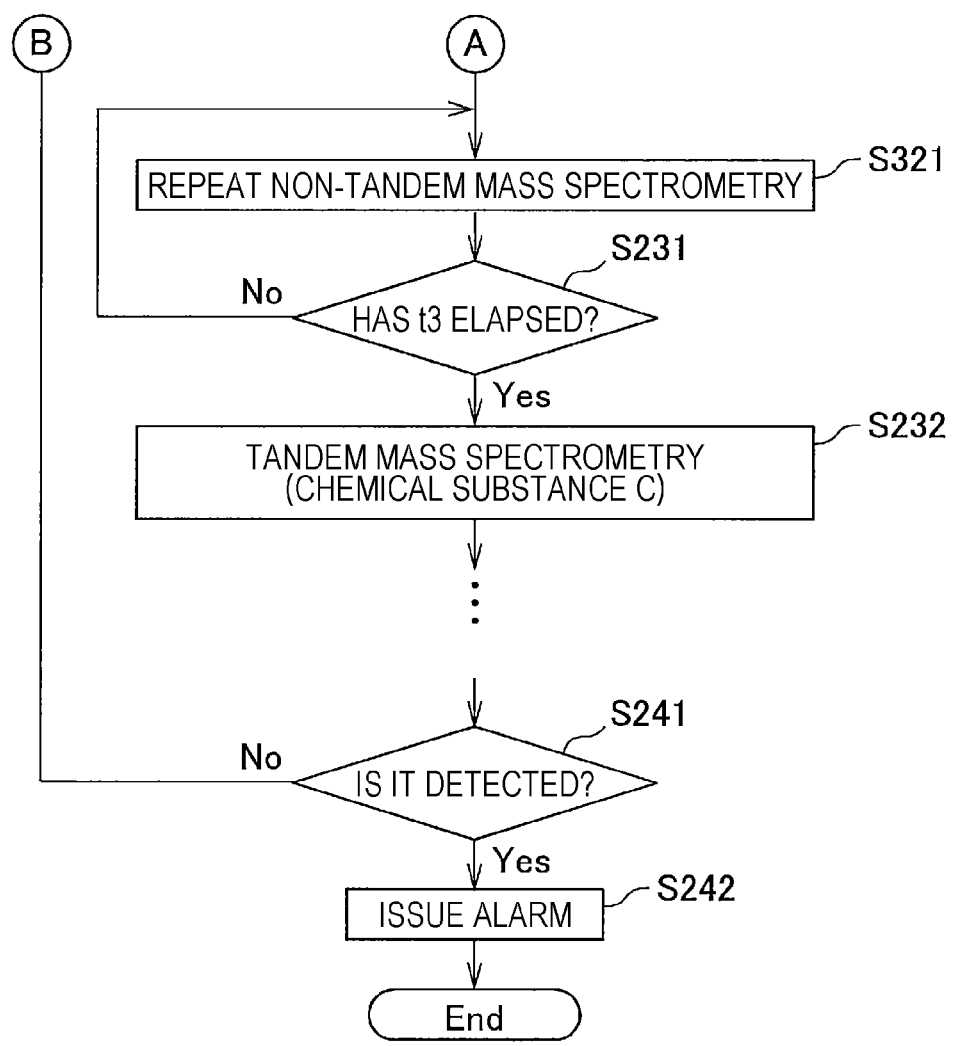
FIG. 14B is a flowchart (part 2) illustrating the procedure of analysis measurement performed in the fourth embodiment.

FIGS. 14A and 14B are flowcharts illustrating a procedure of analysis measurement performed in the fourth embodiment.

In FIGS. 14A and 14B, processes similar to those in FIG. 10 are denoted by the same reference numerals, and description thereof is omitted.

The analysis processing unit 312 causes the mass spectrometer 2 to repeatedly perform the non-tandem mass spectrometry until time t1 elapses from the start of the time measurement in Step S202 (S301 in FIG. 14A).

After completion of the tandem mass spectrometry for "Chemical substance A", the mass spectrometer 2 is used to repeatedly perform the non-tandem mass spectrometry until time t2 elapses from the start of the time measurement in Step S202 (S311).

Then, after the completion of the tandem mass spectrometry for "Chemical substance B", the mass spectrometer 2 is used to repeatedly perform the non-tandem mass spectrometry until time t3 elapses from the start of the time measurement in Step S202 (S321 in FIG. 14B).

As described above, the analysis processing unit 312 repeatedly performs the non-tandem mass spectrometry between the tandem mass spectrometry of a certain chemical substance and the tandem mass spectrometry of another chemical substance.

In Step S241, the analysis processing unit 312 determines "Yes" when a signal indicating an explosive is detected by the tandem mass spectrometry or when a suspicious substance is detected by the non-tandem mass spectrometry.

The soundness of the dangerous object detection system Z can be confirmed by performing the non-tandem mass spectrometry during the time when the tandem mass spectrometry is not performed as described above. This makes it possible to detect an explosive with higher accuracy. In addition, depending on the components of an explosive, the mass spectrum is less likely to show overlap with the impurities in the environment (false reporting is less likely to occur even if determination is made only by the mass spectrum). For such a component, the presence or absence of an explosive component may be determined based on a mass spectrum obtained by the non-tandem mass spectrometry.

In addition, since the tandem mass spectrometry and the non-tandem mass spectrometry can be performed by one mass spectrometer 2 as with the ion-trap mass spectrometer 2a, the processing in the fourth embodiment can be efficiently performed.

Execution Timings of Tandem Mass Spectrometry and Non-Tandem Mass Spectrometry

Figure 15:
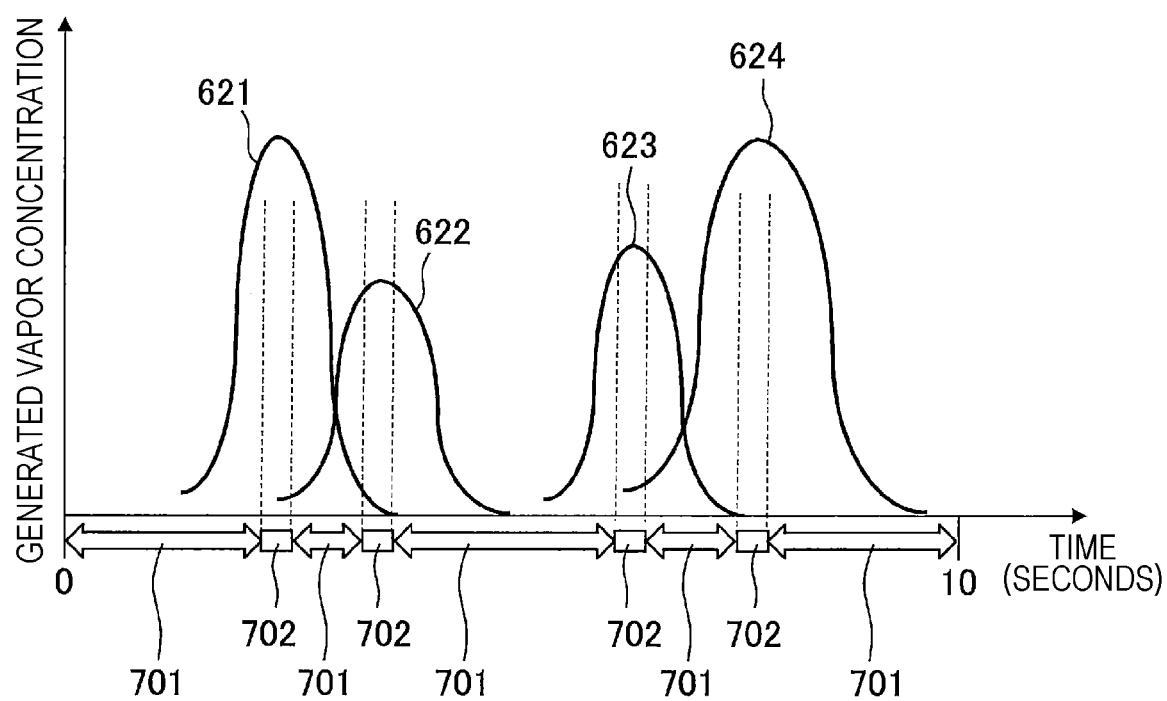
FIG. 15 is a diagram illustrating an example of execution timings of tandem mass spectrometry and non-tandem mass spectrometry.

FIG. 15 is a diagram illustrating an example of execution timings of the tandem mass spectrometry and the non-tandem mass spectrometry.

In FIG. 15, the vertical axis represents the vapor concentration generated, and the horizontal axis represents time (seconds).

In FIG. 15, vapor concentrations of "Chemical substance A" to "Chemical substance D" are schematically illustrated with reference numerals 621 to 624 respectively. Here, it is assumed that the following is true regarding vapor pressures of the chemical substances: vapor pressure of "Chemical substance A">vapor pressure of "Chemical substance B">vapor pressure of "Chemical substance C">vapor pressure of "Chemical substance D". Then, the concentration of each chemical substance is maximized in the following order: "Chemical substance A" (reference numeral 621)→"Chemical substance B" (reference numeral 622)→"Chemical substance C" (reference numeral 623)→"Chemical substance D" (reference numeral 624).

As described above, by heating the wipe material W stepwise in the heater 1, a difference is provided in the timing when the concentration of each chemical component increases. Then, at the timing when the concentration of each chemical substance increases (reference numeral 702), the tandem mass spectrometry is executed upon switching the conditions thereof to those suitable for the chemical substance (with increased concentration). At other times (reference numeral 701), the non-tandem mass spectrometry is repeatedly performed.

In the fourth embodiment, it is assumed that the tandem mass spectrometry and the non-tandem mass spectrometry are performed by the same mass spectrometer 2. However, the present invention is not limited thereto, and the tandem mass spectrometry and the non-tandem mass spectrometry may be performed by different mass spectrometers 2.

Fifth Embodiment

Figure 16A:
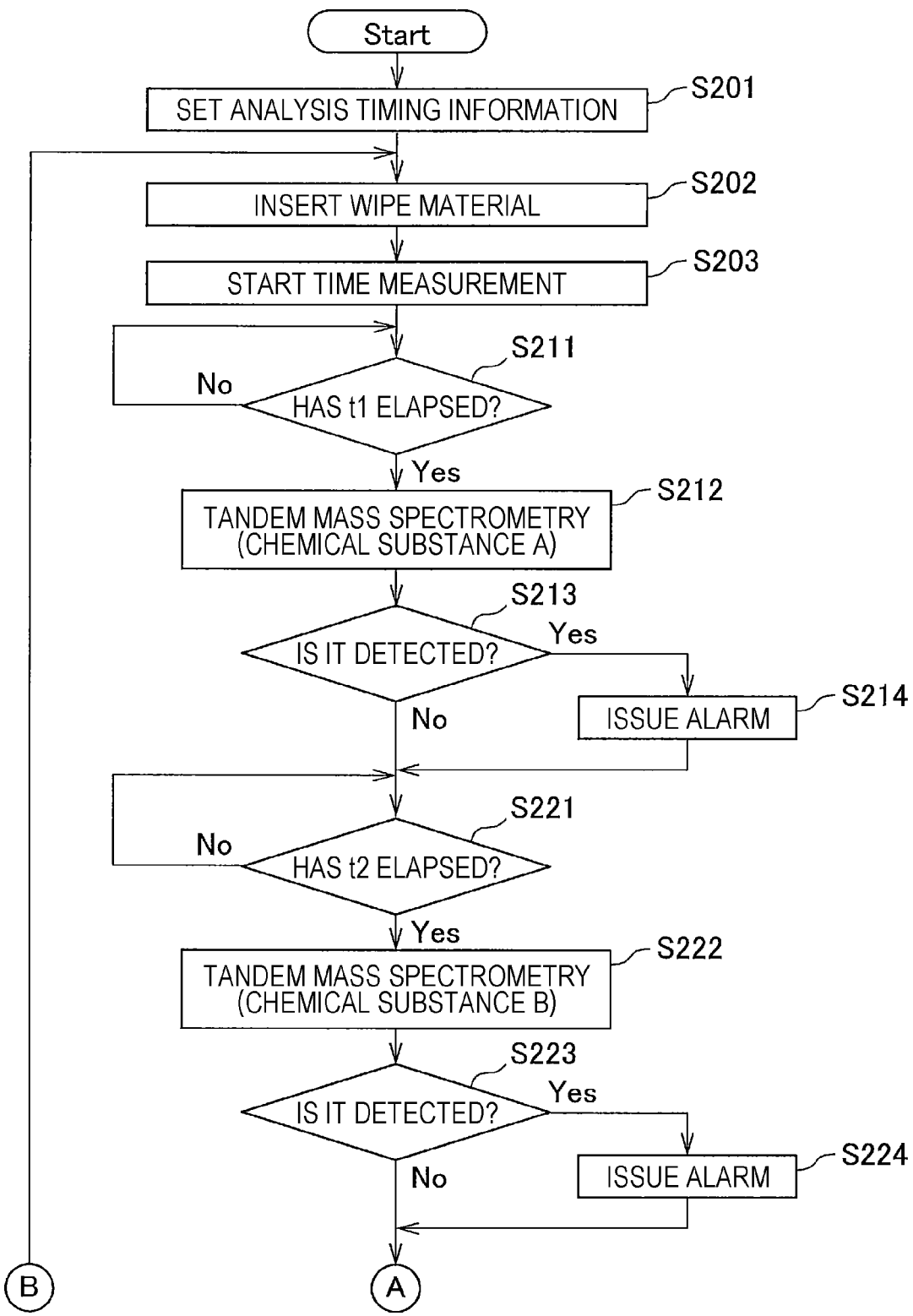
FIG. 16A is a flowchart (part 1) illustrating a procedure of analysis measurement performed in a fifth embodiment.
Figure 16B:
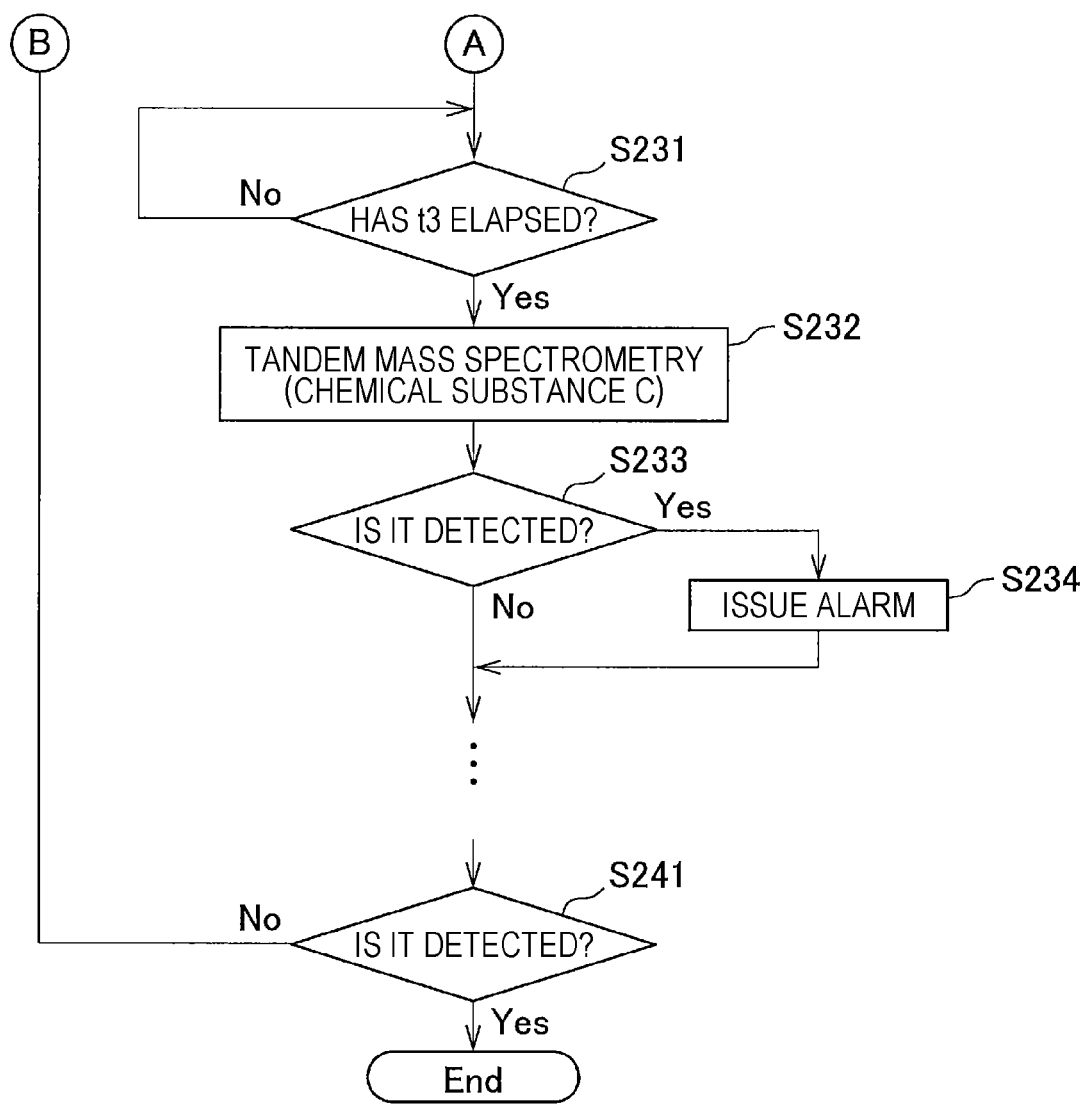
FIG. 16B is a flowchart (part 2) illustrating the procedure of analysis measurement performed in the fifth embodiment.

FIGS. 16A and 16B are flowcharts illustrating a procedure of analysis measurement performed in a fifth embodiment.

In FIGS. 16A and 16B, processes similar to those in FIG. 10 are denoted by the same step numbers, and description thereof is omitted.

After completion of the tandem mass spectrometry for "Chemical substance A" in Step S212 in FIG. 16A, the analysis processing unit 312 determines whether "Chemical substance A" has been detected (S213).

If not detected (No in S213), the analysis processing unit 312 advances the process to Step S221.

When it is detected (Yes in S213), the analysis processing unit 312 causes the alarm issuing device 5 to issue an alarm (S214), and advances the process to Step S221.

In addition, after completion of the tandem mass spectrometry for "Chemical substance B" in Step S222, the analysis processing unit 312 determines whether "Chemical substance B" has been detected (S223).

If not detected (No in S223), the analysis processing unit 312 advances the process to Step S231.

When it is detected (Yes in S223), the analysis processing unit 312 causes the alarm issuing device 5 to issue an alarm (S224), and advances the process to Step S231.

Further, after completion of the tandem mass spectrometry for "Chemical substance C" in Step S232 in FIG. 16B, the analysis processing unit 312 determines whether "Chemical substance C" has been detected (S233).

If not detected (No in S233), the analysis processing unit 312 performs processing relating to the next chemical substance.

When it is detected (Yes in S233), the analysis processing unit 312 causes the alarm issuing device 5 to issue an alarm (S234), and performs processing regarding the next chemical substance.

In this manner, the tandem mass spectrometry is performed for all target chemical substances, and when a target chemical substance is detected, an alarm is issued from the alarm issuing device 5 each time.

When the tandem mass spectrometry and the determination on the presence or absence of the detection is made for all the target chemical substances, the analysis processing unit 312 determines whether any chemical substance among all the target chemical substances has been detected (S241).

When there was no detection (No in S241), the analysis processing unit 312 returns the process to Step S202.

When there was detection (Yes in S241), the analysis processing unit 312 completes the process.

In the process of FIG. 16, the non-tandem mass spectrometry may be repeatedly performed while the tandem mass spectrometry is not performed as in the process of FIG. 14.

Sixth Embodiment

Figure 17:
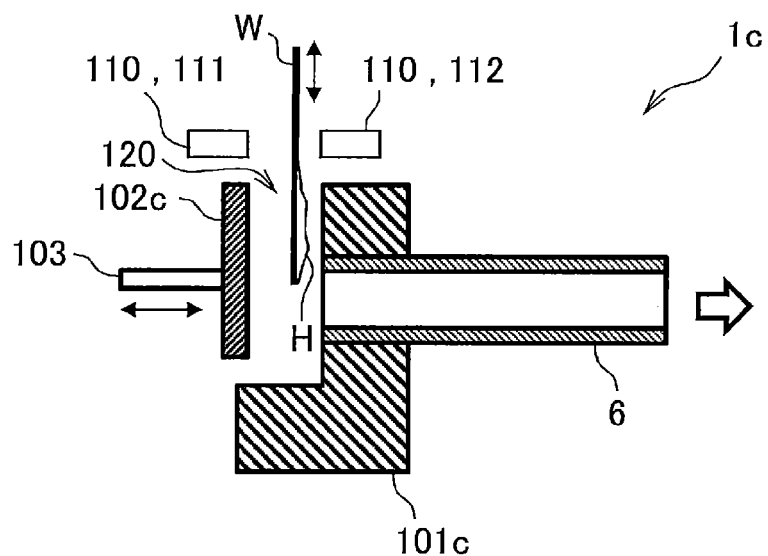
FIG. 17 is a sectional view of a heater used in a sixth embodiment.

FIG. 17 is a sectional view of the heater 1c used in a sixth embodiment.

In FIG. 17, the same components as those in FIG. 2 are denoted by the same symbols, and description thereof will be omitted.

In the heater 1c illustrated in FIG. 17, the temperature of the second heating unit 102c is lower than the temperature of the first heating unit 101c. The operation of the heater 1c is similar to the operation of the heater 1 illustrated in FIG. 2 (that is, the procedure illustrated in FIG. 3). In the heater 1 illustrated in FIG. 2, the temperature of the wipe material W is raised by the temperature of the pressed second heating unit 102. In contrast, in the heater 1c illustrated in FIG. 17, before the second heating unit 102c is pressed, the wipe material W is heated at an intermediate temperature between the second heating unit 102c and the first heating unit 101c. Thereafter, when the second heating unit 102c is pressed, the temperature of the wipe material W is further raised by the heat of the first heating unit 101c onto which the wipe material W is pressed. In FIG. 17, it is desirable that a surface (wiping surface) of the wipe material W to which an attachable matter H is attached faces the first heating unit 101c side. Similarly, in FIG. 2, it is desirable that a surface (wiping surface) of the wipe material W to which the attachable matter H is attached faces the second heating unit 102 side.

Figure 18:
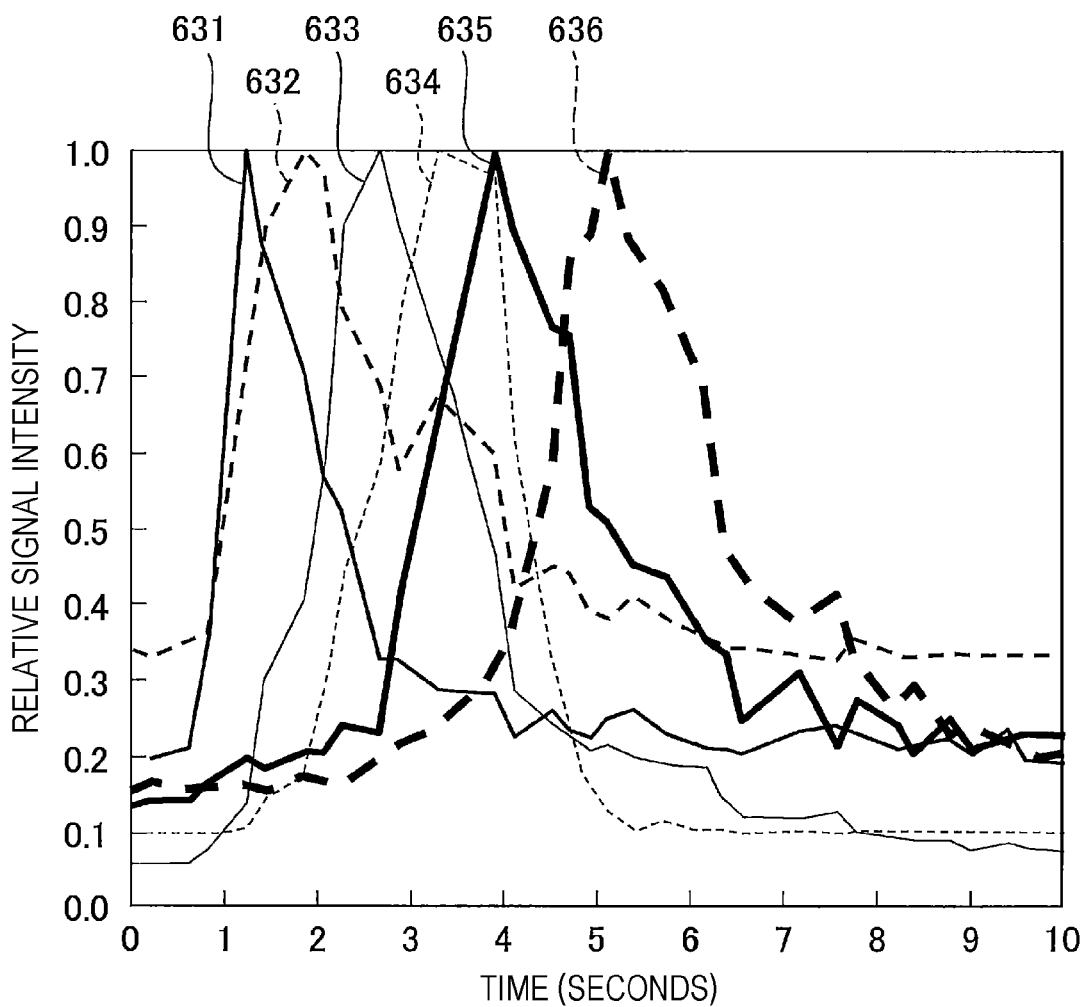
FIG. 18 is a diagram comparing signal appearance times of 6 types of representative explosives.

FIG. 18 is a diagram comparing signal appearance times of 6 types of representative explosives.

Since the signal intensity of each explosive is different, for the sake of clarity, comparison has been made in terms of relative signal intensity with the maximum intensity of 1 for each explosive. That is, in FIG. 18, the vertical axis represents relative signal intensity, and the horizontal axis represents time (seconds).

As a result, it can be seen that the maximum values of the signals of acetone peroxide (TATP) denoted by reference numeral 631, nitroglycerin (NG) denoted by reference numeral 632, trinitrotoluene (TNT) denoted by reference numeral 633, penthrite (PETN) denoted by reference numeral 634, ammonium nitrate (AN) denoted by reference numeral 635, and hexogen (RDX) denoted by reference numeral 636 appear in order at intervals of about 0.5 seconds to 1 second. Therefore, based on the temporal change of the signal intensity illustrated in FIG. 18, the tandem mass spectrometry for TATP is performed 1.2 seconds after the insertion of the wipe material W. Thereafter, the tandem mass spectrometry may be executed at appropriate times for NG, TNT, PETN, AN, and RDX in that order.

As described above, experiments have shown that the detection accuracy is improved as illustrated in FIG. 18 by including the heater 1c illustrated in FIG. 17.

Further, the present invention is not limited to the above embodiments, and various modifications may be included. For example, the above-described embodiments of the invention have been described in detail in a clearly understandable way, and are not necessarily limited to those having all the described configurations. A configuration of a certain embodiment may partly be replaced with a part of the configuration of another embodiment. A part of the configuration of another embodiment may be added to the configuration of an embodiment. In addition, a part of the configuration of each embodiment may be omitted, replaced with another configuration, or added with another configuration.

In each embodiment, the wipe material W is inserted into the heater 1, but any other medium may be used as long as a chemical substance adheres thereto. For example, a filter or the like used in a predetermined device may be inserted into the heater 1.

In each embodiment, the first heating unit 101 is heated to about 100° C. in advance. However, the present invention is not limited thereto, and the heating may be made to a temperature other than 100° C. (for example, 80° C., 200° C., or the like) according to the chemical substance to be analyzed. The same applies to the second heating unit 102 In each embodiment, the second heating unit 102 is heated to about 200° C. However, the present invention is not limited thereto, and the temperature may be other than 200° C. (160° C., 300° C., etc.) as long as the temperature is higher than the first heating unit 101.

The results of tandem mass spectrometry and the results of non-tandem mass spectrometry may be stored in the database 4. As a result, the analysis timing information 401 and the preliminary analysis information can be updated.

In addition, as the mass spectrometer 2 in each embodiment, a mass spectrometer of Patent Literature 2 that simultaneously selects a plurality of types of ions and simultaneously dissociates these selected ions may be applied.

In addition, some or all of the above-described configurations, functions, units 311 and 312, database 4, storage device 322, or the like may be realized by hardware, for example, by designing with an integrated circuit. In addition, as illustrated in FIG. 6, each of the above-described configurations, functions, or the like may be realized by software by a processor such as the CPU 321 interpreting and executing a program for realizing each function. Information of the program realizing functions, tables, or files may be stored in a recording device such as a memory or a Solid State Drive (SSD) or a non-transitory storage medium such as an Integrated Circuit (IC) card, a secure digital (SD) card, or a Digital Versatile Disc (DVD) instead of being stored in the HD.

Further, in each embodiment, only control lines and information lines considered to be necessary for explanation are illustrated, and not all the control lines and the information lines for a product are necessarily illustrated. In practice, almost all the components of a configuration may be considered to be connected to each other.

REFERENCE SIGNS LIST 1, 1a to 1c Heater (medium heater)
2 Mass spectrometer (tandem mass spectrometer, non-tandem mass spectrometer)
2a Ion-trap mass spectrometer (tandem mass spectrometer, non-tandem mass spectrometer)
3 Control device (controller)
4 Database (storage)
5 Alarm issuing device (alarm activation unit)
101 First heating unit (high temperature portion, low temperature portion)
101a First heating unit (medium insertion unit)
102 Second heating unit (high temperature portion, low temperature portion)
120 Insertion portion (gap)
121 Electric heater (heating unit, heater unit)
130 Infrared device (heating unit, infrared irradiation unit)
131 Infrared lamp (heating unit, infrared irradiation unit)
401 Analysis timing information
t1 to t3 Heating time (elapsed time)
t11 Time (predetermined time, first predetermined time) from start of time measurement t12 Predetermined time
t13 Predetermined time (second predetermined time)
W Wipe material (medium)
Z Dangerous object detection system (substance analyzer)

The invention claimed is:

1. A substance analyzer, comprising:
a medium heater configured to heat a medium for collecting a chemical substance adhering to a surface of an inspection object;
a tandem mass spectrometer configured to perform tandem mass spectrometry of vapor derived from the chemical substance sent from the medium by being heated and vaporized by the medium heater;
a controller configured to cause the tandem mass spectrometer to perform, based on a temperature of the medium in the medium heater, the tandem mass spectrometry for the chemical substance that is vaporized at the temperature of the medium using the vapor sent from the medium heater to the tandem mass spectrometer; and
a storage configured to store analysis timing information in which an elapsed time measured based on a time at which the medium is inserted into the medium heater is associated with information regarding for which chemical substance the tandem mass spectrometry is performed at the elapsed time, wherein
the analysis timing information is based on data on the chemical substance obtained in advance with a temperature rise of the medium heater that is consistent, and
the controller is further configured to:
measure a heating time of the medium heater based on a time at which the medium is inserted into the medium heater; and,
in response to the measured heating time reaching the elapsed time in the analysis timing information, cause the tandem mass spectrometer to perform the tandem mass spectrometry for the chemical substance that is associated with the elapsed time in the analysis timing information.

2. The substance analyzer according to claim 1, wherein the medium heater includes a high temperature portion and a low temperature portion, the low temperature portion being configured to have a lower temperature than a temperature of the high temperature portion,
the medium is inserted into a gap between the high temperature portion and the low temperature portion,
the medium is maintained in the gap for a predetermined time, and
after the predetermined time has elapsed, the medium is sandwiched between the high temperature portion and the low temperature portion.

3. The substance analyzer according to claim 2, wherein the medium is sandwiched between the high temperature portion and the low temperature portion by pressing the high temperature portion against the low temperature portion after the predetermined time has elapsed.

4. The substance analyzer according to claim 2, wherein the medium is sandwiched between the high temperature portion and the low temperature portion by pressing the low temperature portion against the high temperature portion after the predetermined time has elapsed.

5. The substance analyzer according to claim 1, wherein the medium heater includes:
a heating unit configured to gradually heat the medium.

6. The substance analyzer according to claim 5, wherein the medium heater includes:
a medium insertion portion configured to allow the medium to be inserted therein; and
a heater unit configured as the heating unit to heat the medium together with the medium insertion portion, and
after the medium is inserted into the medium insertion portion, the heater unit gradually increases the temperature according to time.

7. The substance analyzer according to claim 5, wherein the medium heater includes:
an infrared irradiation unit configured as the heating unit to irradiate the medium with an infrared ray.

8. The substance analyzer according to claim 1, further comprising:
an alarm activation unit configured to activate an alarm when a target chemical substance is detected by the tandem mass spectrometry.

9. The substance analyzer according to claim 1, further comprising:
a non-tandem mass spectrometer configured to perform mass spectrometry of vapor derived from the chemical substance vaporized by the medium heater, the non-tandem mass spectrometer performing mass spectrometry by non-tandem mass spectrometry and not by the tandem mass spectrometry,
wherein the controller is further configured to
perform the mass spectrometry by the non-tandem mass spectrometer while the tandem mass spectrometry is not being performed.

10. The substance analyzer according to claim 9, wherein the tandem mass spectrometer and the non-tandem mass spectrometer are included in the same apparatus.

11. A substance analysis method, wherein:
a storage unit is provided to store analysis timing information in which an elapsed time measured based on a time at which a medium is inserted into a medium heater is associated with information regarding for which chemical substance a tandem mass spectrometry is performed at the elapsed time, the analysis timing information being based on data on the chemical substance obtained in advance with a temperature rise of the medium heater that is consistent, and
the substance analysis method includes:
heating, by the medium heater, a medium for collecting a chemical substance adhering to a surface of an inspection object;
causing, by a controller, a tandem mass spectrometer to perform, based on a temperature of the medium in the medium heater, tandem mass spectrometry for a chemical substance that is vaporized at the temperature of the medium using vapor sent from the medium heater to the tandem mass spectrometer by: measuring a heating time of the medium heater based on a time at which the medium is inserted into the medium heater; and instructing, in response to the measured heating time reaching the elapsed time in the analysis timing information, the tandem mass spectrometer to perform the tandem mass spectrometry for the chemical substance that is associated with the elapsed time in the analysis timing information; and
performing, by the tandem mass spectrometer, the tandem mass spectrometry for a chemical substance as instructed by the controller by performing the tandem mass spectrometry for the chemical substance that is associated with the elapsed time.

12. The substance analysis method according to claim 11, wherein
the medium heater includes:
- a high temperature portion; and
    - a low temperature portion configured to have a lower temperature than a temperature of the high temperature portion, and
- the substance analysis method further includes:
- when the medium is inserted into a gap between the high temperature portion and the low temperature portion, maintaining, by the medium heater, the medium in the gap for a first predetermined time;
    - after the first predetermined time has elapsed, sandwiching, by the medium heater, the medium between the high temperature portion and the low temperature portion; and
- after the tandem mass spectrometry is completed and the medium is removed from the medium heater, bringing, by the medium heater, the high temperature portion and the low temperature portion into contact with each other for a second predetermined time.

* * * * *